United States Patent
Choi et al.

(10) Patent No.: US 11,191,937 B2
(45) Date of Patent: *Dec. 7, 2021

(54) METHODS AND SYSTEM FOR ULTRASONIC TARGETED DRUG DELIVERY IN CYSTIC FLUIDS, SUCH AS THE CEREBROSPINAL FLUID, USING BUOYANCY SPECIFIC DRUG CARRIERS

(71) Applicant: Advanced CSF Therapies, LLC, Mineola, NY (US)

(72) Inventors: Jae H. Choi, Mineola, NY (US); Keith Baker, Danvers, MA (US); Alexander Klose, New York, NY (US); John Pile-Spellman, Pelham, NY (US)

(73) Assignee: Advanced CSF Therapies, LLC, Mineola, NY (US)

( * ) Notice: Subject to any disclaimer, the term of this patent is extended or adjusted under 35 U.S.C. 154(b) by 166 days.

This patent is subject to a terminal disclaimer.

(21) Appl. No.: 16/360,153

(22) Filed: Mar. 21, 2019

(65) Prior Publication Data

US 2020/0086104 A1 Mar. 19, 2020

Related U.S. Application Data

(63) Continuation of application No. 15/190,896, filed on Jun. 23, 2016, now Pat. No. 10,258,781.

(60) Provisional application No. 62/271,045, filed on Dec. 22, 2015, provisional application No. 62/183,444, filed on Jun. 23, 2015.

(51) Int. Cl.
*A61M 31/00* (2006.01)
*A61M 37/00* (2006.01)
*A61B 17/34* (2006.01)
*A61M 27/00* (2006.01)

(52) U.S. Cl.
CPC ..... *A61M 37/0092* (2013.01); *A61B 17/3401* (2013.01); *A61M 27/006* (2013.01); *A61M 2210/1003* (2013.01)

(58) Field of Classification Search
CPC .......... A61K 41/0028; A61M 37/0092; A61M 2210/1003; A61M 27/006; A61N 7/00; A61B 2017/22088; A61B 17/3401
See application file for complete search history.

(56) References Cited

U.S. PATENT DOCUMENTS

| 2003/0215394 A1* | 11/2003 | Short ................. | A61K 9/1617 424/9.52 |
| 2008/0089912 A1* | 4/2008 | DiMauro ............. | A61K 9/0009 424/400 |
| 2014/0142468 A1* | 5/2014 | Hossack ............ | A61B 17/2202 601/2 |

\* cited by examiner

*Primary Examiner* — Rebecca E Eisenberg
(74) *Attorney, Agent, or Firm* — Antonio Papageorgiou; Lombard Geliebter LLP

(57) ABSTRACT

A method for delivering drugs into cystic fluid, the method comprising injecting a drug delivery system (DDS) into a cystic fluid space at an injection site, the DDS comprising at least one therapeutic agent encapsulated in biodegradable polymers, applying ultrasonic energy proximal to the injection site, and controlling the at least one of buoyancy, delivery location, mixing, and dispersion of the DDS to a targeted area using the ultrasonic energy.

20 Claims, 13 Drawing Sheets

| | Oral Rx | Pellet Implant | Endovascular RX (Experimental) | Intrathecal-ventricular Rx | ACSFT (lumbar CSF) |
|---|---|---|---|---|---|
| Clinical Use | Standard of Care | Experimental | In use/Experimental | In use/Experimental | *Proposed/Experimental* |
| Neuroprotective Rx | Nimodipine | Nimodipine/Nicardipine PRI | Vasodilators (high doses) | Thrombolytics/Vasodilators | *Thrombolytics/Vasodilators DDS* |
| Access | Oral | Neurosurgery | Femoral+Carotid Artery | Cranial Borehole | *Lumbar Puncture* |
| Earliest Timing of Rx | Anytime | With surgery (clipping) | With angiography (coiling) | With ventricular probe (borehole) | *Anytime (lumbar puncture/drainage)* |
| Administration | Systemic | Local | Local | Local | *Local* |
| Drug Concentration at Site | low | High (programmable drug release) | High | High | *High (programmable drug release)* |
| Primary Effected Sites | Systemic | Intracranial SAS | Intracranial Arterial | CSF/Ventricles | *CSF/Intracranial SAS* |
| Extended Drug Release | No | Yes | No | Difficult/No | *Yes* |
| Local Thrombolysis | No | Yes/Irrigation | No | Yes | *Yes* |
| Local Vasodilators | No | Yes | Yes | Yes | *Yes* |
| Repeatability | Very easy | | | | |
| Setting | ER or Floor | OR | OR | ICU or OR | *ER or Floor* |
| Professional Group | Emergency Med/Neurology/ Internal Med | Neurosurgery | Endovascular Neurology/ Radiology | Neurosurgery/ Intensive Care | *Emergency Med/Neurology/ Radiology/ Internal Med* |
| Resource Need | Very low | Very High | High | High | *Low* |
| Invasiveness | Very low | Very High | High | High | *Low* |
| Complexity | Low | Very High | High | High | *Low* |
| Principal Adverse Effects Type | Systemic | Surgical/Systemic | Surgical | Local | *To be determined* |
| Clinical Evidence | RCT (nimodipine) | Case Series, small RCT (nicardipine) | Case Series (vasodilators) | Case Series (thrombolytics and vasodilators) | *To be determined* |
| Efficacy | RCT (nimodipine) | TBD | Case Series | Case Series | *To be determined* |

ACSFT (Advanced CSF Therapies, LLC); CSF (cerebrospinal fluid); DDS (drug delivery system); ER (emergency room); ICU (intensive care unit); OR (operating room); PRI (prolonged release implant); RCT (randomized controlled trial); RX (therapy); SAS (subarachnoid space).

FIG. 1

| Disease conditions of "cysts": Solved by direct cyst Injection: Factors challenging drug delivery | Cerebral Spinal Fluid Space | Solution by ultrasound directed mixing (USx) | Solution by slow release (SR) | Solution by buoyancy and ultrasound directed drug carrier (BD) |
|---|---|---|---|---|
| Critical drug concentration (narrow therapeutic range) | +++++ | ++++ | ++++ | ++++ |
| Long drug dosing duration required | +++ | - | - | - |
| Large volume of fluid in cyst | ++++ | ++++ | - | - |
| Extensive length/geometry of cystic cavity | +++++ | ++++ | +++++ | +++++ |
| Bulk flow gradients along cystic cavity must be overcome | +++ | +++ | +++++ | +++++ |
| Specific gravity gradients of drug vs cyst that must be overcome | +++ | +++ | +++++ | +++++ |
| Complex multi pseudo compartments | ++++ | +++++ | + | + |

Fig. 2

|  | USx | SR | BD | USx + SR | USx + BD | SR + BD | USx + SR + BD |
|---|---|---|---|---|---|---|---|
| Critical drug concentration (narrow therapeutic range) | ++ | +++ | ++ | +++++ | + | ++ | +++++ |
| Long drug dosing duration required |  | ++++ |  |  |  | +++ | + |
| Large volume of fluid in cyst | +++ |  | ++ |  | ++++ |  | +++ |
| Extensive length/geometry of cystic cavity | +++ |  | ++ | ++ | ++++ | ++ | +++++ |
| Bulk flow gradients along cystic cavity must be overcome | ++ |  | ++ | ++ | ++++ | + | +++++ |
| Specific gravity gradients of drug vs cyst that must be overcome | ++ |  | ++ | ++ | +++ | ++ | +++++ |
| Complex multi pseudo compartments | +++ |  |  | +++++ | ++++ |  | +++++ |
| Visual dose estimation/ Confirmation | +++ |  |  | +++ | +++ |  | +++ |

| CSF space | Characteristic | Drug target requirements | Characteristics: Nimodipine | Characteristics: tPA |
|---|---|---|---|---|
| 1) Volume | 150 cc | 1) Dose | TBD | TBD |
| 2) Shape | Long and narrow (circa 30 inches, and ¼ inch across, | 2) Duration | 14 days | Hours to days |
| 3) Internal compartments | Two large compartments septated | 3) Possible cumulative toxicity | None | Yes |
| 4) Specific gravity of the fluid, | 1.003 | 4) Off target drug toxicity | Low (hypotension when given systemically) | TBD (expected to be low as confined to CSF) |
| 5) Estimated bulk flow | 500-600 cc/day | 5) Partition coefficient | High for target (lipophilic) | High for blood clot |
| 6) Patient position | Head up, head down, decubitus, flexed head to gain access to ventricles | 6) Drug carrier specific gravity | Buoyant | Buoyant |
| 7) Cyst entry cite determined | Lumbar puncture or Intraventricular | 7) Drug carrier stable against US energy | Yes | Yes |
| 8) Acoustic window | LP-fair; Sub Occipital- good; Intra- ventricular- poor | 8) Vehicle size | TBD | TBD |

METHODS AND SYSTEM FOR ULTRASONIC TARGETED DRUG DELIVERY IN CYSTIC FLUIDS, SUCH AS THE CEREBROSPINAL FLUID, USING BUOYANCY SPECIFIC DRUG CARRIERS

CROSS REFERENCE TO RELATED APPLICATION

This application claims the priority of U.S. Provisional Application No. 62/183,444, entitled "METHODS AND SYSTEM FOR TARGETED DRUG DELIVERY IN CEREBROSPINAL FLUID USING BUOYANCY SPECIFIC DRUG CARRIERS," filed on Jun. 23, 2015, the disclosure of which is hereby incorporated by reference in its entirety.

BACKGROUND OF THE INVENTION

The present application relates to methods and drug delivery systems for targeted drug delivery, and more particularly for ultrasonic targeted delivery using buoyancy specific drug carriers.

Drug delivery into cystic structures, such as the cerebrospinal fluid (CSF) space, specifically spinal CSF canal, urinary or gallbladder, ocular compartments, or thoracal and abdominal cavities, offers unique opportunities and challenges. High concentration of drug in the target space with good mixing leads to spectacular therapeutic results. This is seen in treatment of bacterial cystitis, where antibiotics are given systemically, e.g. intravenous or oral administration, are then concentrated by the kidney and delivered to the inflamed urinary bladder, making only a short course of antibiotics needed. In contrast, the major challenge in drug delivery to the CSF by routine systemic routes, is the existence of physiological barriers, i.e., blood brain barrier and brain liquor barrier that prevent drugs from accumulating in therapeutic concentrations at the target sites. This is evident in the case of subarachnoid hemorrhage (SAH) where blood and blood byproducts accumulate in the CSF, in the cerebral subarachnoid space and at the base of the brain causing inflammatory reactions, cerebral vasospasm, and impairment of cerebral microcirculation. The principal therapy standard is obliteration of the ruptured aneurysm by endovascular coiling or surgical clipping. However, the removal of blood, the causative agent for potentially deleterious complications, from the CSF and treatment of the effects thereof has been challenging. This is because relevant drugs mostly do not sufficiently penetrate the physiological barriers or have severe side effects when given systemically. Similarly, treatment of infectious, inflammatory, or neoplastic diseases affecting cystic structures, e.g. intraocular, intrapleural, intraperitoneal, intracholecystic, and intravesical cavities, could be safer and more efficacious when therapeutics would be given locally and distributed more effectively leading to high drug concentration at the target sites while minimizing systemic side effects. Accordingly, there is a need for methods and systems for the delivery of drugs that are not so limited.

SUMMARY OF THE INVENTION

This patent application describes novel methods and system using ultrasound and buoyancy modified drug carrier for enhanced drug delivery that may control one or more of the following: A) Location of the drug (i.e., guided delivery throughout the targeted areas), B) Mixing of the drug into the target areas, and C) Dispersion of the drug modifications or the drug or carriers in cystic media.

To achieve sufficient concentrations of drugs within cystic cavities at the target site and at the same time to avoid unwanted systemic effects, a direct injection of drugs into the cystic space may be necessary. Cystic fluid has intrinsically slow internal mixing and partitions primarily by gravity slowly over time. Substantial mixing of the different fluid locations only occurs through external forces, which may include lavage, repositioning of patient, ballottement, and shaking. All ionic drugs when dissolved in water-like body fluids are hyperdense, whereas all lipophilic drugs tend to be hypodense. The specific gravity of CSF is low, ranging between 1.003-1.008 at 37° C., as compared to that of whole blood, which ranges between 1.048-1.054, and plasma, which ranges between 1.019-1.022. Transudates have lower protein content and lower specific gravity compared to exudates (<0.015 vs. >0.015). The specific gravity of the drug solution may be modified by varying the amount of glucose it contains, i.e. higher glucose content leads to a hyperbaric solution (relative to CSF).

In this regard, the novel method for controlled buoyancy, delivery, mixing, and/or dispersion of drugs/drug carriers generally involves obtaining information regarding the density/specific gravity of the fluid of the target area, such as the specific gravity of CSF. The targeted area, e.g. base of the brain, may then be identified and the buoyancy of the drug or drug delivery system may then be adjusted/selected, based on the predetermined density/specific gravity of the fluid. That is, the drug or drug delivery system may be adjusted so that it is positive, negative, or neutrally buoyant in the target fluid. The drug may then be introduced into the cavity, e.g. lumbar CSF space and the subject's body positioned as needed. External ultrasound may then be applied to the injection site (or proximal to the injection site) to control/assure adequate mixing of the drug or drug delivery system within the CSF. External ultrasound energy may then be applied to direct the drug or drug delivery system toward the target location, thus accelerating the drug delivery to the target tissue. The ultrasound energy thereby creates a directional current of the cystic fluid which will carry the drug delivery system to the target location. Focused ultrasound in the range of 1-8 MHz, or preferably in the range of 1.7-2.5 MHz may be used and the area insonated for a duration that is routine for clinical diagnostic studies ensuring safe energy exposure to tissue and minimizing fragmentation of the delivery system.

It is understood that various drugs may be delivered using the method(s) discussed herein, including without limitation calcium channel inhibitors (CCI), such as nimodipine and nicardipine, growth factors, such as erythropoietin (EPO), fibrinolytic substances, such as tissue plasminogen activator (tPA), statins, neuroprotectants, antimicrobials, steroidal and non-steroidal anti-inflammatory agents, anti-neoplastic chemotherapeutics, and immune-modulating drugs, among others. For instance, in the case of SAH, CCI, tPA, and statins are desirable substances due to proven efficacy (CCI), capability to dissolve blood clots (tPA), and proven neuroprotective effects (CCI, statins). Although the method(s) are discussed herein in relation to CSF and treating SAH, it is understood that the steps are applicable to treat other conditions and other targeted areas within cystic structures, e.g. for intravesical, intrapleural, intraperitoneal, or intraocular administration.

According to one embodiment, a method for delivering drugs into cystic fluid comprises injecting a drug delivery system (DDS) into a cystic fluid space at an injection site, the DDS comprising at least one therapeutic agent encapsulated in biodegradable polymers, applying ultrasonic energy proximal to the injection site, and controlling the at least one of buoyancy, delivery location, mixing, and dispersion of the DDS to a targeted area using the ultrasonic energy.

The method may further comprise guiding delivery of the DDS to the targeted area using the ultrasonic energy. A directional current of the cystic fluid may be created using the ultrasonic energy to deliver the DDS to the targeted area. The biodegradable polymers may be any one of neutrally, negatively, or positively buoyant in water. In one embodiment, the method further comprises selecting buoyancy of the DDS based on a density or specific gravity of the cystic fluid. According to another embodiment, buoyancy of the DDS may be selected based on one or more characteristics of the at least one therapeutic agent, therapeutic agent requirements, and the target area.

In yet another embodiment, the DDS may be localized using ultrasonic imaging. The ultrasonic energy may be in the range of 1-8 MHz. The ultrasonic energy may also be applied in pulsed-wave mode. The at least one therapeutic agent can be selected from a group consisting of calcium channel inhibitors, growth factors, fibrinolytic substances, statins, neuroprotectants, antimicrobials, steroidal anti-inflammatory agents, non-steroidal anti-inflammatory agents, anti-neoplastic chemotherapeutics, and immune-modulating drugs.

Additional aspects of the present invention will be apparent in view of the description which follows.

BRIEF DESCRIPTION OF THE DRAWINGS

FIG. 1-5 depict charts that compare the benefits of ultrasound guided drug delivery systems for cystic structures and the various methods for treating SAH.

DETAILED DESCRIPTION OF THE INVENTION

Figure 5:
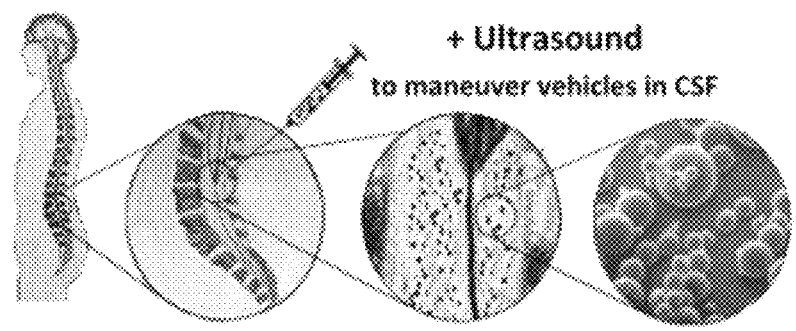
Figure 6A:
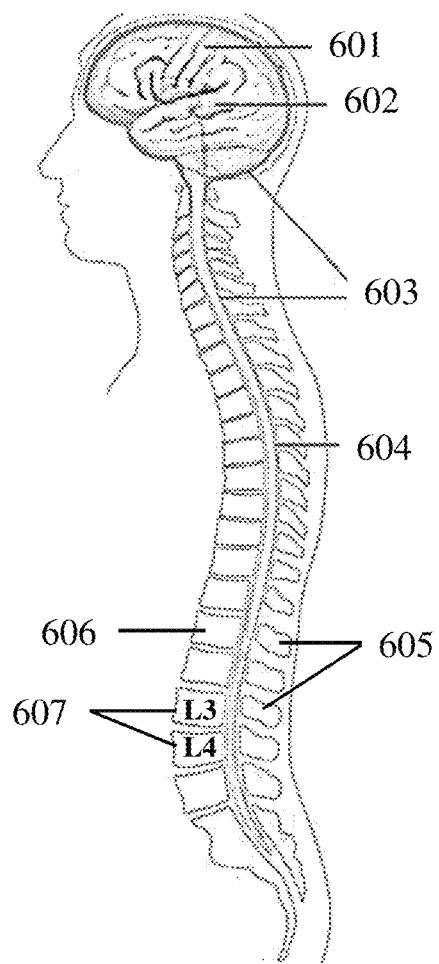
FIGS. 6A and 6B depict anatomy and a process for collecting cerebrospinal fluid (CSF) according to one embodiment of the methods discussed herein.
Figure 6B:
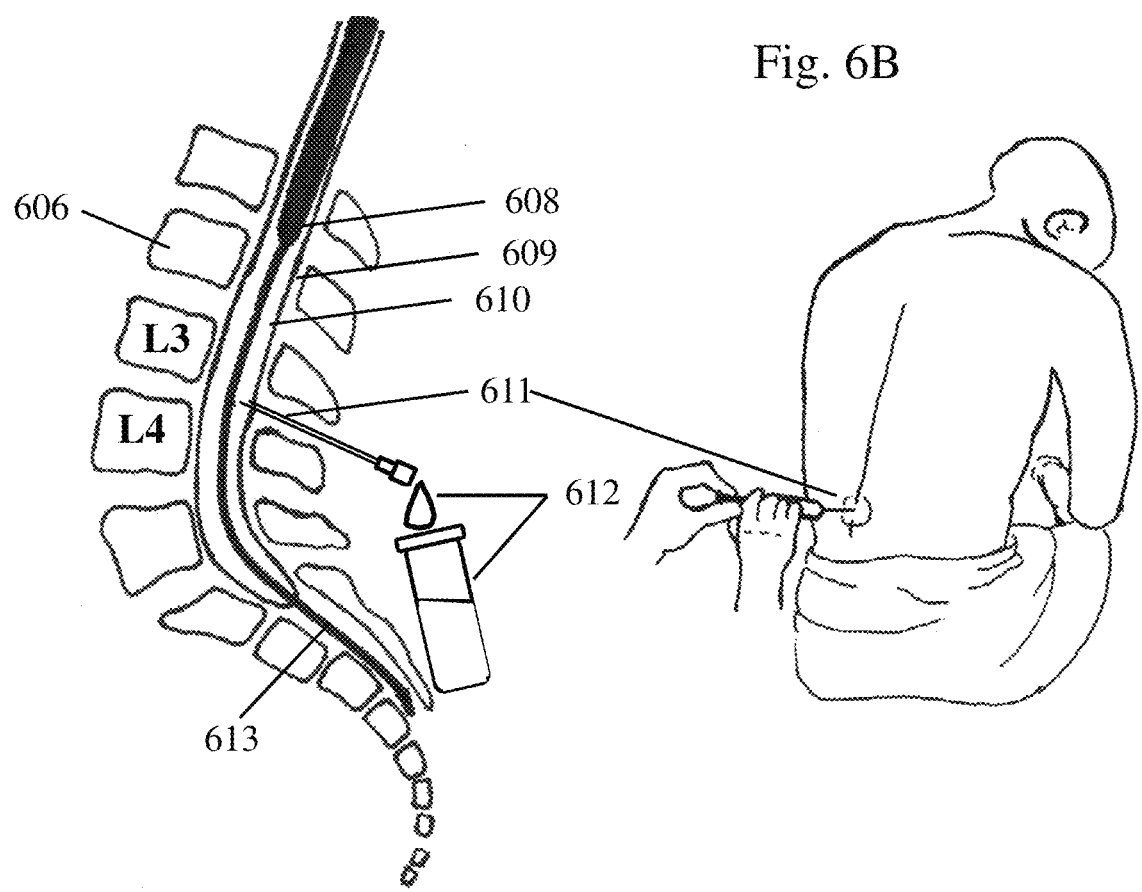
Figure 7:
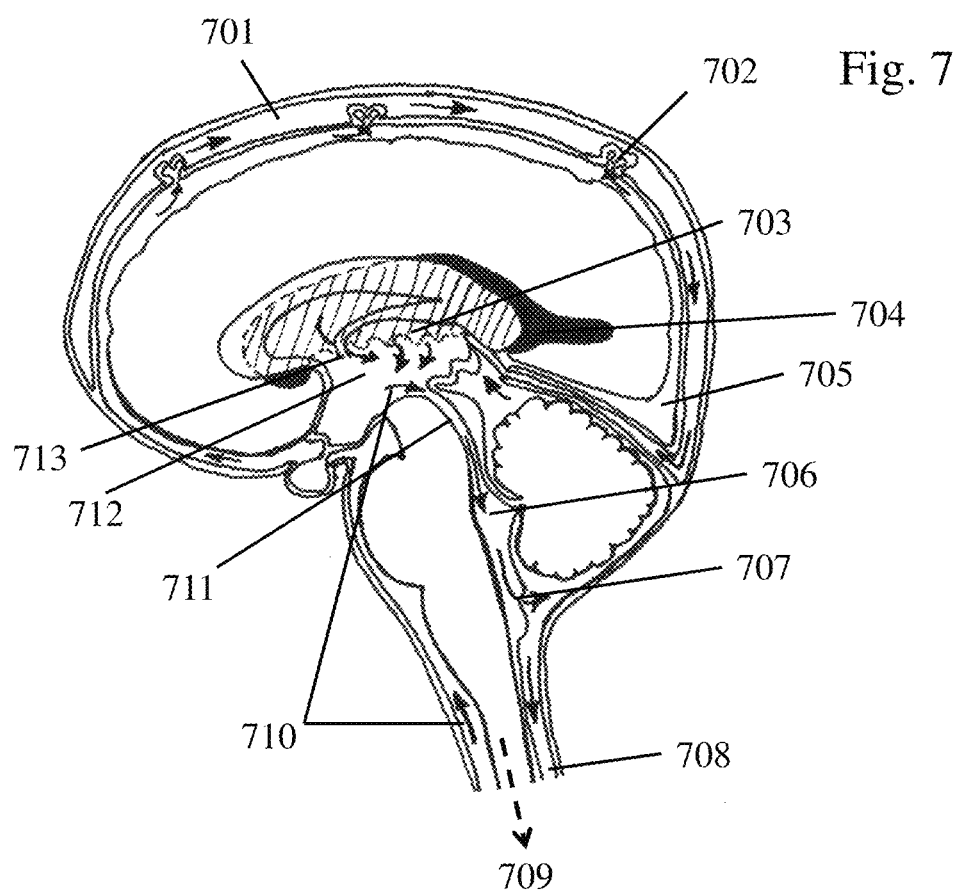
FIG. 7 depicts CSF flow within the central nervous system.

With an annual incidence of Ser. No. 10/100,000, intracranial aneurysmal subarachnoid hemorrhage (SAH) occurs in approximately 30,000 people in the US per year. Despite improvement in the management of SAH in the last decades, 30-day case fatality ranges between 29-45% and up to 67%, albeit with considerable regional and study-dependent variability. Furthermore, among survivors, more than 50% are left with significant disability after 30 days and 1 year. It has been recognized that initial bleed and recurrent bleed account for the majority of cases with poor outcome. Thus, the primary focus of early management is on the eradication of the ruptured aneurysm with surgical clipping or endovascular coil embolization.

Still, many survivors of SAH are faced with complications that typically occur within the first 2 weeks from aneurysm rupture. Delayed cerebral ischemia (DCI) is one of the most common and serious complications that occurs in approximately 30% of survivors and is responsible for 40% of poor outcome in this group. DCI is often a diagnosis after exclusion of other causes and is supported with evidence from brain imaging such as computed tomography (CT) and magnetic resonance imaging (MRI). Some feared consequences of DCI include focal neurological deficits, neurological deterioration, cognitive decline, death, and long-term disability. There are several potential causes for DCI, such as vasospasm, i.e. narrowing of proximal and distal arteries, inflammation, neurodegeneration, and impairment of cerebral microcirculation and autoregulation. The common underlying cause is considered to be the presence of blood and blood breakdown products in the subarachnoid space following aneurysm rupture. In fact, subarachnoid blood has been found to predict DCI and poor outcome (death or severe disability) in several studies, including a meta-analysis of 1,355 SAH patients from the placebo arms of randomized controlled trials.

Historically, vasospasm has received much attention as the patency (or lack thereof) of cerebral vessels could be well described with conventional angiograms. Such vessel narrowing also offered a plausible explanation to neurological deficits and cerebral ischemia or infarcts caused by perfusion deficit. Although vasospasm-associated DCI is a fearful combination, it has been shown that angiographically confirmed vasospasm is not necessarily associated with clinical symptoms and poor. Conversely, detrimental outcome has been observed despite the absence of vasospasm suggesting other factors might contribute to the cerebral injury cascade, such as impaired microcirculation and autoregulation, and inflammation. It is known that calcium channel inhibitors and nitrous oxide donors have a spasmolytic effect on vascular smooth muscle cells. As such, the most frequent adverse reaction of vasodilators is decrease in blood pressure. Interestingly, early administration of oral nimodipine, a calcium channel inhibitor and the only pharmacological therapy with proven efficacy in SAH, has been found to improve outcome (relative risk of poor outcome 0.67; 95% CI-0.55-0.81 versus placebo), but not vasospasm itself. Nicardipine, another calcium channel blocker, on the other hand, reduced vasospasm, but was not associated with better outcome.

In contrast to systemic administration, local delivery of drugs allows to achieve high drug concentrations at the site of interest. Vasodilators have been infused into the brain vasculature by endovascular means in SAH patients, with early clinical results suggesting effectivity in reducing vasospasm. Furthermore, with several hundred patients studied (using mostly the drug nicardipine), intrathecal administration of vasodilators through ventricular shunts has also shown promising results regarding their ability to prevent vasospasm. However, both endovascular and intrathecal approaches have not yet undergone randomized controlled trials.

Considering the fact that the cause of the potentially deleterious complications of aneurysm rupture is the blood, its components, and byproducts in the subarachnoid space, another attractive therapeutic option would be to lyse the clot. Thrombolytics, such as urokinase and recombinant tissue plasminogen activator have been used for surgical cisternal irrigation, and (often repeated) intrathecal administration with and without cisternal drainage following aneurysm rupture and repair. Although preliminary results showed that clot clearance could be accelerated and vasospasm reduced with local thrombolytics, the risk was also increased for shunt-dependent hydrocephalus and meningitis. Other less effective or inconclusive systemic drug interventions include endothelin-1 receptor antagonist (clozasentan), magnesium, statins, nonglucocorticoid aminosteroid (trilazad), anticoagulants and antiplatelets.

In an attempt to maximize and also extend the duration of the neuroprotective effect of calcium channel inhibitors investigators have studied the clinical safety and efficacy of surgically implanting pellets filled with nimodipine or nicardipine-containing vehicles (prolonged release implants or PRI). Hereby, nimodipine or nicardipine are encapsulated in biocompatible and biodegradable microspheres or vehicles made from polymers, such as poly(lactide-co-glycolic acid) or PLGA, so-called drug delivery systems, and packed into small dissolving pellets that are then implanted in the subarachnoid space adjacent to major cerebral vessels. The vast majority of clinical reports on >300 SAH patients are about the experience with nicardipine PRI. However, systematic clinical studies investigating the safety and efficacy of intracranial nimodipine PRI in SAH patients are underway. The advantages of this surgical approach are 1) the pellets can be implanted immediately following surgical clipping, 2) the drug is released slowly and over an extended duration, both of which can be programmed through customized composition of the PLGA spheres, 3) the drug is released locally at the site of interest (cerebral vessel) achieving high site-specific concentrations, and 4) the entire drug delivery system is metabolized over time. The disadvantages are the necessity for invasive surgery, increased requirement of hospital resources, increased cost of the procedure, inability to adjust the dose after implantation without repeated surgery, and yet uncertain efficacy of the procedure to improve outcome.

Current pharmacological standards and experimental procedures in the treatment of SAH-related complications include oral, intra-arterial, intraventricular, and surgical administration. All forms have drawbacks in one or more of the following categories: invasiveness of administration, drug specificity and drug concentration ratio target:non target site, side effects, timing and duration of drug release, mechanism, efficacy, and extent of resource utilization and cost. FIG. 1 provides a table that compares the positive and negatives of these procedures and the procedures proposed herein.

In this context, the present application provides a novel approach for delivering drugs and drug delivery systems into the cerebrospinal fluid (CSF) using direct injection, that also address the challenges associated with such direct injection into the CSF with controlled buoyancy, delivery, mixing, and/or dispersion of drugs/drug carriers using ultrasonic techniques.

The factors limiting drug delivery into the target brain site after direct injection into the CSF may include one or more of the following: A. Critical drug concentration (narrow therapeutic range), B. Effective drug concentration at the target site, C. Extensive length of cystic cavity (spinal CSF canal) requiring transport of the drug, D. Bulk flow gradients along cystic cavity must be overcome, E. Specific gravity gradients of drug vs. CSF space that must be overcome, F. Large volume of fluid in CSF. Additional challenges when using ultrasound include necessity to limit the energy exposure to tissue to ranges that are clinically safe and to avoid or minimize the destruction or fragmentation of the drug or drug delivery system.

These challenges can be overcome by ultrasound enhanced mixing, slow drug release mechanisms, and controlled buoyancy and ultrasound directed drug/drug carriers/delivery system, in combination with ultrasound applications that are routine for clinical diagnostic or therapeutic procedures. Ultrasound at low clinical frequency ranges, i.e. 1.0-4.0 MHz have a benign energy profile and can be used over several minutes in vivo, e.g. for transcranial Doppler to study brain vessels or during pregnancy for fetal ultrasound examinations. When ultrasound energy at those frequency ranges is focused and directed toward fluids, such as water, this leads to co-directional movement of the fluid. With this movement of the fluid, carriers, such as drug delivery systems, can be transported through cystic structures, such as the spinal CSF, that have a low fluid turnover (more hydrostatic than hydrodynamic). As can be seen from the chart in FIG. 2, the CSF space is challenging for drug delivery and the one where the methods discussed herein offer multiple solutions to these problems.

In addition, low frequency focused ultrasound moves the fluid, not the drug carrier directly, meaning the drug carrier does not have to be acoustically active. Secondly, low to moderate energy ultrasound applied in pulsed-wave mode will avoid or minimize tissue damage and the destruction or fragmentation of the carrier ensuring sufficient carrier quantity reaches the target location by sustenance of physical integrity of the drug delivery system during transport. Lastly, simultaneous B-Mode ultrasound imaging allows visual monitoring of the location, quantity, and integrity of the drug delivery system within the cystic medium.

The drug carrier/delivery system for ultrasound and/or the combination of ultrasound and buoyancy directed therapies may include microspheres (vehicles/carriers) to facilitate the movement of drug in the CSF to the target area. The benefits of using microspheres in this respect are shown in FIG. 3, noted by the grey areas. It is understood that other vehicles may be used and the invention is therefore not limited thereto.

In general, drug carrier/delivery system (DDS) may be biocompatible, biodegradable, have a programmable release profile, and be able to deliver drugs to the injured (target) site. With the DDS herein, gravitational forces are partly countered by vehicles that have neutral or positive buoyant properties. DDS consists of a biodegradable polymer composition and a therapeutic agent or therapeutic agents. DDS may have negative, neutral or positive buoyant properties by their composition or by addition of a buoyancy agent (U.S. Pat. Nos. 6,123,956 and 8,367,116 B2, which are incorporated herein).

Preliminary Results: Polymer Characteristics, Fabrication and Testing: The physical properties and proven biocompatibility of poly(lactide-co-glycolides) copolymers (PLGA) make them the most extensively studied commercially available clinical and biodegradable polymers. PLGA is soluble in organic solvents and naturally degrades in water by bulk hydrolysis of ester linkages to yield the monomeric constituents lactic and glycolic acids.

Lactate converted into pyruvate and glycolate enter the Krebs cycle to be degraded into $CO_2$ and $H_2O$. The rate of PLGA hydrolysis controls the rate of release of an encapsulated pharmaceutical. Thus, the release of a drug in a PLGA matrix is controlled by varying the polymer's lactide: glycolide ratio and molecular weight. Also, by controlling various process parameters (i.e. solvent/non-solvent systems, shear rate during emulsification or hardening) it is possible to control the size of the microspheres. This is important, microsphere size and composition may affect the distribution of the microspheres in the CSF. The buoyancy agent may be used to ensure free movement of the microspheres throughout the CSF space. Non-buoyant PLGA micro-particles aggregate to form a large mass resulting in a net decrease of surface area and increased variability of the release rate. The proper buoyancy—positive, neutral, or negative—of spheres minimizes the likelihood of collision and/or aggregation which also can interfere with their degradation, i.e. when spheres flow more freely, collision is minimized.

Microsphere Movement in Water with Ultrasound: Focused ultrasound energy from transducers at the lower frequency spectrum as in use for clinical diagnostic or therapeutic purposes (1.0-8.0 MHz) is sufficient to move non-dynamic fluid, such as the CSF and with this, solid materials within the fluid, such as polymer microspheres. Our preliminary research with polyethylene (100 μm diameter) and trisacryl (cross linked with gelatin) microspheres (200 μm) showed instantaneous and rapid particle movement with the ultrasonic-directed water.

Safety of PLGA Microspheres and Intrathecal Drugs: The FDA has approved DDS products made of PLGA (e.g. Lupron Depot, Trelstar Depot, and Nutropin Depot). PLGA has a well-defined 25-year safety history for parenteral applications. Studies on PLGA microsphere safety in the human brain have been restricted to intracerebral administrations into the striatum and placement into the cranial CSF space. Clinically, intrathecal drug delivery has been routinely used in pain medicine or studied in patients using various drugs, e.g. opioid and non-opioid analgesics, muscle relaxants, thrombolytics, calcium channel blockers and other vasodilators.

In one embodiment, therapeutic agents are encapsulated in polymers that are biodegradable and are neutrally (float in medium) or positively buoyant (updrift) in water. The DDS may also be isodense and/or radio opaque relative to the CSF. The DDSs are injected into the lumbar CSF space allowing the drug to be released into the extracellular space of the brain on a controlled and sustained basis (FIG. 5). Therefore, DDS are maneuvered with safe clinical grade ultrasound energy to the brain site of interest minimizing transit time through the CSF space and accelerating site specific release of drugs. Simultaneous B-Mode duplex ultrasound imaging would also allow the localization of the buoyant microspheres that have a contrasting effect.

It is further believed that proper buoyancy would allow the microspheres to remain at and adhere to the target location, the base of the brain, dissipate locally and release the loaded drug in quantity and time according to the polymer composition. A comparison of clinically relevant characteristics of different modes of pharmacological neuroprotective treatment in patients with the disclosed treatment method (ACSFT) according to embodiments of the present invention is shown in FIG. 1.

Generally, each case/treatment can be tailored to address key considerations. For example, the drug(s) appropriate for the clinical scenario will need to be chosen. Information regarding drug target requirements may correspondingly be collected, such as: 1) Dose, 2) Duration, 3) Possible cumulative toxicity, 4) Off target toxicity, 5) Partition coefficient, 6) Drug carrier specific gravity, 7) Drug carrier stable against US energy, and/or 8) Vehicle size.

Figure 8:
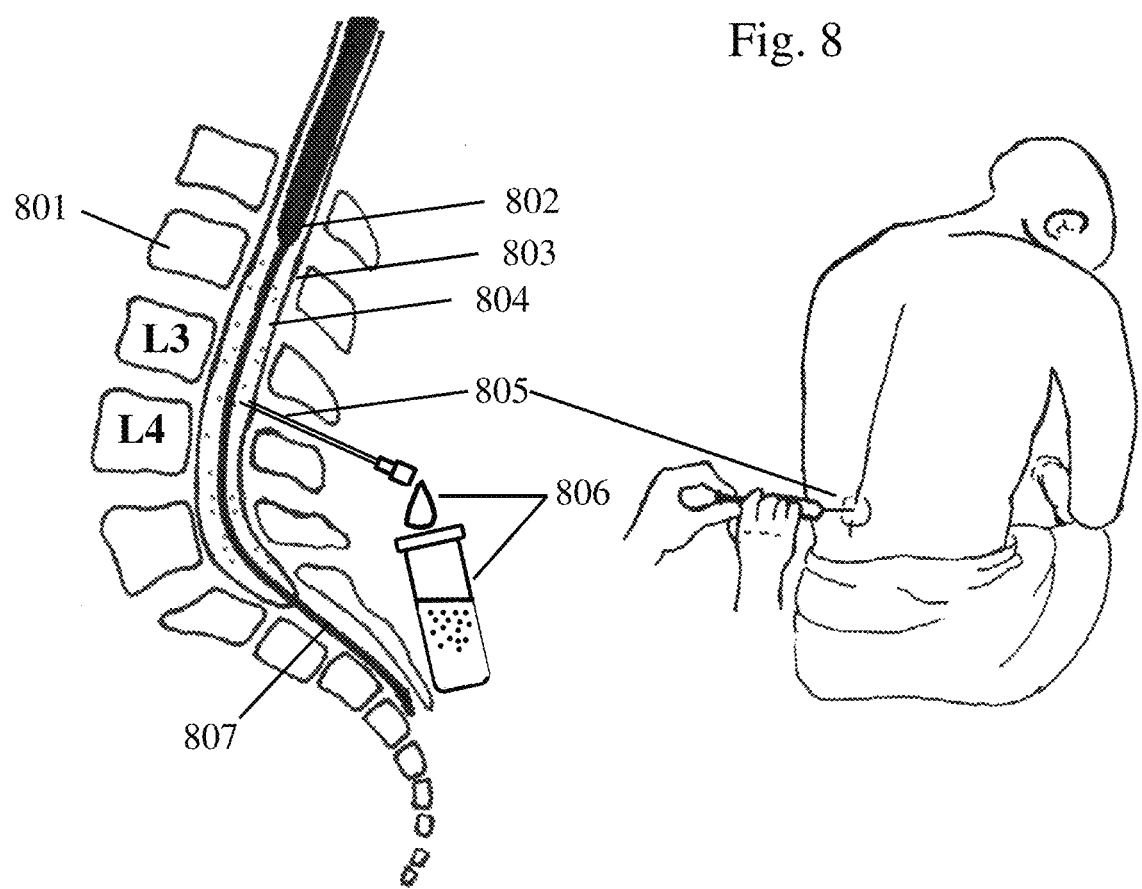
FIG. 8 depicts a process for collecting blood in (CSF) according to one embodiment of the methods discussed herein.

Moreover, the characteristics of the treatment area may also be considered. For instance, key characteristics of the CSF space, in general or for a particular subject, may be considered, including: 1) Volume, 2) Shape, 3) Internal compartments, 4) Specific gravity of the fluid, 5) Estimated bulk flow (usually negligible), 6) Position of the patient, 7) Lumbar access, 8) Target site(s), and/or 9) Acoustic window.

From the injection site at the lower lumbar space to the basal cisterns in the brain, there is a distance of approximately 40-50 cm in the 70 kilo person that the drug or drug carriers must travel. Finally, the buoyancy of the drug/drug carrier is considered/selected based on one or more of the characteristics of the drug, drug requirements, and target area. The buoyancy is related to the intrinsic buoyancy of the specially designed microsphere and the amount and density of the medication, and gravity.

Exemplary treatment or prevention in this patent application is for Subarachnoid Hemorrhage related vasospasm and delayed cerebral ischemia with nimodipine and/or tPA loaded buoyancy and ultrasound. Data for this/these embodiment(s) is provided in the table shown in FIG. 4. It is understood that the methods discussed herein may be used for the treatment and/or prevention of other conditions.

Optimal case specific calculation of buoyancy and drug doses in combination with US-guided delivery of the vehicles to the target site allows that the patient need not be kept bolt upright or head-down or be forced to positional changes for extended periods after the injection. Additionally, early trapping and adherence to surrounding tissues during travel to target site is less likely to happen due to both, buoyancy and US-enhanced guidance. Specifically, with US-enhanced guidance, the delivery time is expected to be brief, within minutes, after which the vehicles will distribute and adhere along the walls of the target site to release the drug(s) according to their pre-programmed release profile.

The drug dose and quantity of microspheres depend on the following factors: 1) drug concentration at target site, 2) half-life of the drug, 3) drug release profile, 4) duration of drug release, 5) drug carrying capacity per microsphere, 6) estimated volume of target space.

In this regard, the method(s) for treating/preventing a condition, such as those related to SAH, with controlled buoyancy, delivery, mixing, and/or dispersion of drugs/drug carriers generally involves selecting a drug for the clinical scenario. Thereafter, the density/specific gravity of the fluid of the target area, such as the specific gravity of CSF, may be determined (FIG. 6A-8) and the buoyancy of the drug or drug delivery system may then be adjusted/selected, based on the predetermined density/specific gravity of the fluid. FIG. 6A and FIG. 6B presents a process for collecting CSF via a spinal tap. The brain 601, lateral ventricle 602, cerebrospinal fluid 603, spinal cord in cerebrospinal fluid 604, spinous processes 605, vertebral body 606, and lumbar vertebral bodies (L3 and L4) 607, conus medullaris 608, thecal sack 609, intrathecal space 610, lumbar puncture 611, collection of cerebrospinal fluid 612, and cauda equine 613 are illustrated. FIG. 7 illustrates CSF made in lateral ventricle 704 and flowing out Foramen of Monro 713, CSF 710 flowing out third ventricle 712 through cerebral aqueduct 711 and fourth ventricle 706, CSF 710 flowing out of fourth ventricle 706 through bursa and Magendie into median aperture and basal subarachnoid space (SAS) 707, intrathecal space 708 along spinal cord 709, and CSF flow from superior sagittal sinus 701, choroid plexus 703, SAS over cortex 705, and arachnoid granulations 702. FIG. 8 illustrates vertebral body 801, conus medullaris 802, thecal sack 803, blood in intrathecal or spinal subarachnoid space 804, lumbar puncture 805, collection of blood in cerebrospinal fluid 806, and the cauda equina 807. Blood in spinal subarachnoid space 804 is collected in the cerebrospinal fluid (xanthochromia) 806. The density/specific gravity of the drug/drug delivery system may be selected so that relative to the fluid at the target area, the drug/drug delivery system is positively, negatively, or neutrally buoyant. In this regard, a plurality of drugs/drug delivery systems with a common therapeutic agent may be provided each with a different density so that the physician can select the prepared drug/drug delivery system at that time for the desired buoyancy.

Figure 9:
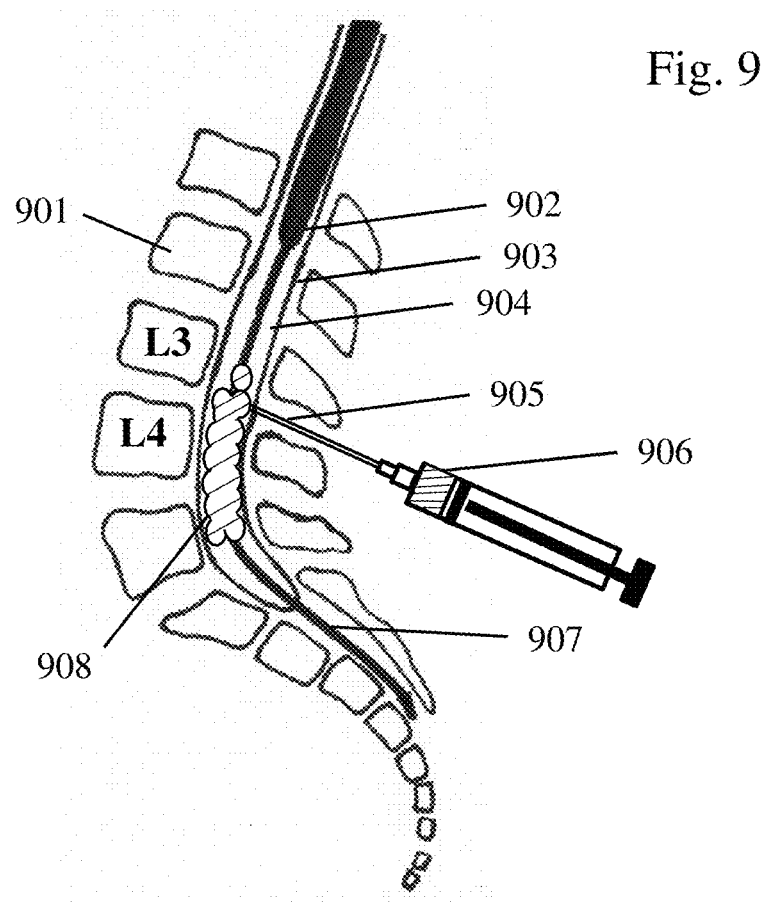
FIG. 9 depicts flow of normal hyperbaric drugs/drug delivery systems in the lumbar cavity.
Figure 10:
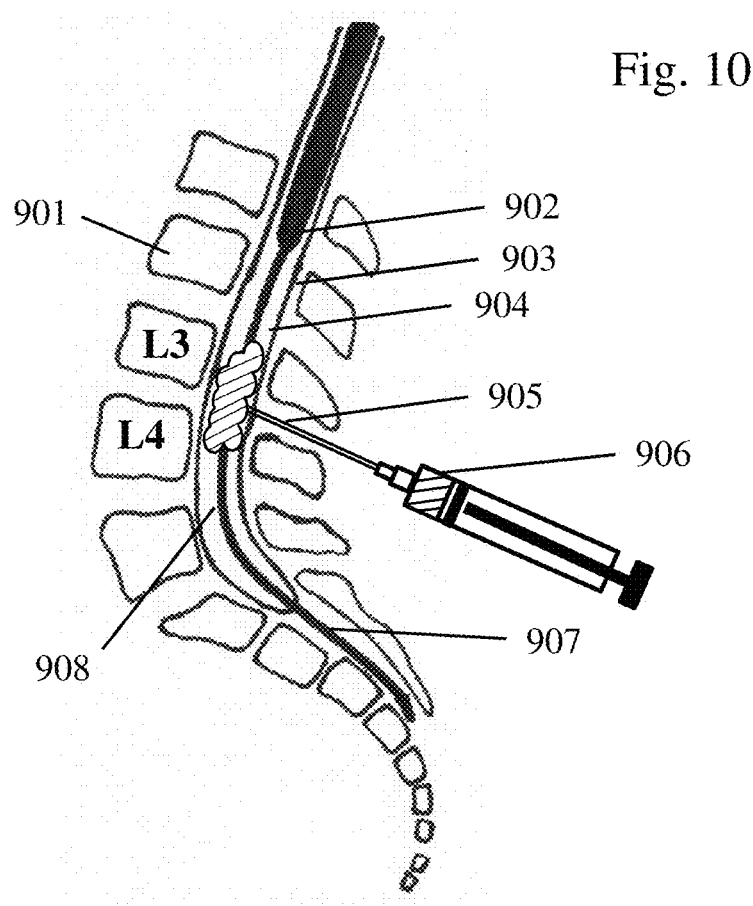
FIG. 10 depicts a process for direct injection of normal isobaric or hypobaric drugs/drug delivery systems into the lumbar cavity according to an embodiment of the methods discussed herein.
Figure 11:
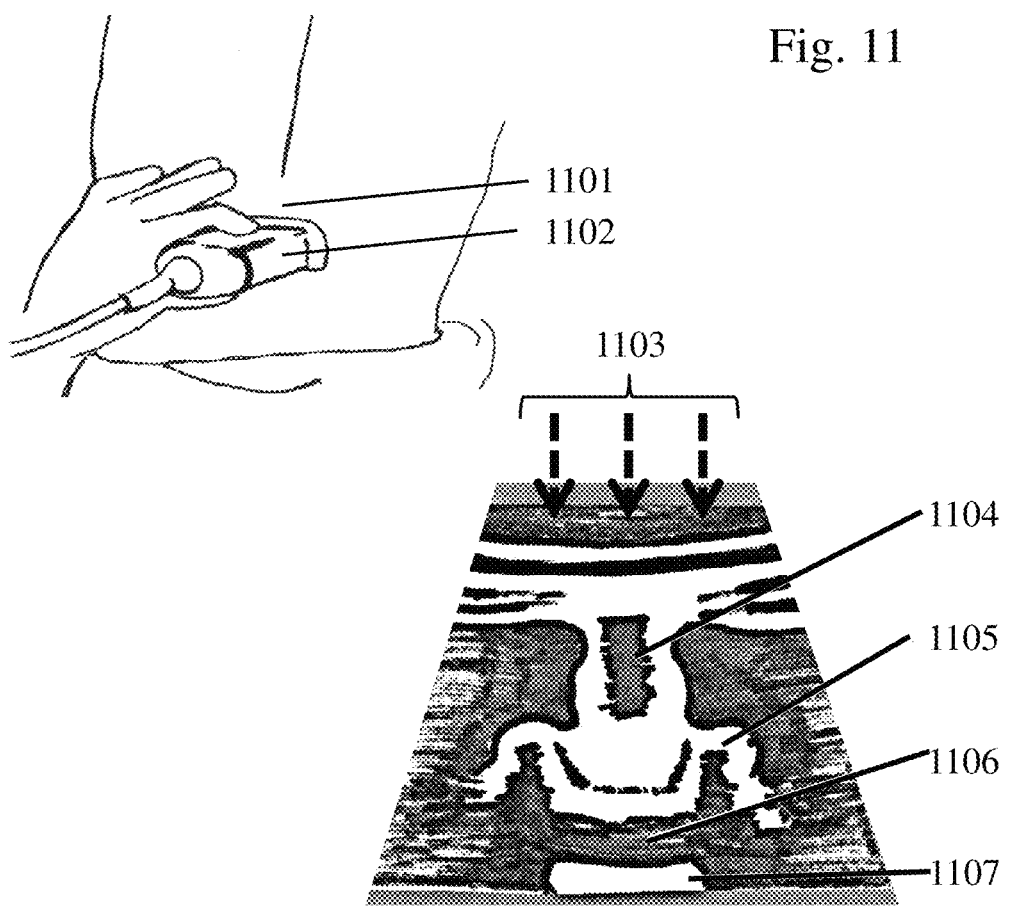
FIG. 11 depicts the application of ultrasound energy to the lumbar region, proximal to the injection site according to an embodiment of the methods discussed herein.
Figure 12:
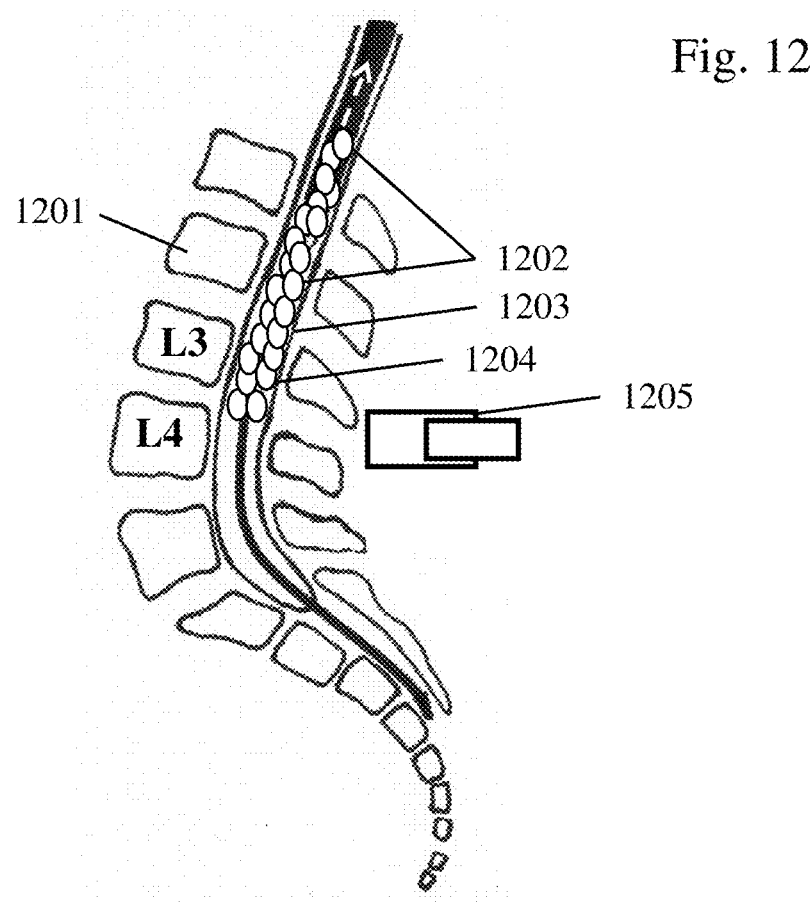
FIG. 12 depicts the mixing/agitation, and acceleration of drugs/drug delivery systems to the brain as a result of applying ultrasound energy to the lumbar region according to an embodiment of the methods discussed herein.

FIGS. 9 and 10 presents a vertebral body 901, conus medullaris 902, thecal sack 903, intrathecal space 904, lumbar puncture 905, hyperdense drug 906, cauda equina 907, and distribution of the drug in cerebrospinal fluid 908. The targeted area, e.g. base of the brain, may then be identified and the drug 906 introduced into the lumbar cavity (FIG. 9-10) by direct injection 905 of the drug/drug delivery system and the subject's body positioned as needed (normal hypertonic medication injected into SAH setting in posturally dependent localiar and hypotonic medication flowing cephalad but becoming caught by intrathecal structures, such as roots and arachnoid) for the application of ultrasound energy to, among other things, mix, disperse, and/or direct, guide, and/or accelerate the drug/drug carrier within the cavity, toward the target area, as the case may be (FIGS. 11-12). FIG. 11 illustrates an ultrasound transducer 1102 placed on a lumbar region 1101. A direction of ultrasound energy and B-mode image can produce spinal structures seen on ultrasound of interspinous ligament 1104, articular process 1105, intrathecal space 1106, and posterior vertebral body 1107. FIG. 12 illustrates a vertebral body 1201 and medication being mixed in the intrathecal space 1204 and carried by ultrasound energy 1205 through thecal sack 1203 towards the targeted area 1202, e.g. base of the brain. In one embodiment, the subject's body may be position so that it is not upright, e.g., so that the head is located even or lower relative to the injection site, which may reduce the need for a hypotonic carrier, making the focused ultrasound the primary enabling technology for guiding the DDS to the site of interest.

While the foregoing invention has been described in some detail for purposes of clarity and understanding, it will be appreciated by one skilled in the art, from a reading of the disclosure that various changes in form and detail can be made without departing from the true scope of the invention.

What is claimed is:

1. A method for delivering drugs into cystic fluid, the method comprising:
    injecting a drug delivery system (DDS) into a cystic fluid space at an injection site, the DDS comprising at least one therapeutic agent encapsulated in biodegradable polymers;
    applying ultrasonic energy proximal to the injection site; and
    controlling the at least one characteristic of the DDS; and creating a directional current of the cystic fluid using the ultrasonic energy therewith delivering the DDS to a target area through the cystic fluid space.

2. The method of claim I further comprising guiding delivery of the DDS to the targeted area using the ultrasonic energy.

3. The method of claim 1 further comprising selecting buoyancy of the DDS based on a density or specific gravity of the cystic fluid.

4. The method of claim 3, wherein the DDS is negatively buoyant relative to the cystic fluid.

5. The method of claim 3, wherein the DDS is neutrally buoyant relative to the cystic fluid.

6. The method of claim 1 further comprising selecting buoyancy of the DDS based on one or more characteristics of the at least one therapeutic agent, therapeutic agent requirements, and the target area.

7. The method of claim 1 further comprising localizing the DDS using ultrasonic imaging.

8. The method of claim 1 wherein the ultrasonic energy is in the range of 1-8 MHZ.

9. The method of claim 1 wherein the ultrasonic energy is applied in pulsed-wave mode.

10. The method of claim 1 wherein the at least one therapeutic agent is selected from a group consisting of calcium channel inhibitors, growth factors, fibrinolytic substances, statins, neuroprotectants, antimicrobials, steroidal anti-inflammatory agents, non-steroidal anti-inflammatory agents, anti-neoplastic chemotherapeutics, and immune-modulating drugs.

11. The method of claim 1, wherein the DDS is non-destructively delivered to the targeted area using the ultrasonic energy.

12. The method of claim 11, wherein buoyancy of the DDS is such that the DDS remains at the target area with the ultrasonic energy removed.

13. The method of claim 11, wherein the DDS provides extended release of the therapeutic agent, the method comprising adhering the DDS to the target area for extended release thereto.

14. The method of claim 1, wherein the at least one characteristic of the DDS comprises at least one of buoyancy, delivery location, mixing, and dispersion of the DDS to a targeted area using the ultrasonic energy.

15. A method for delivering drugs into cerebrospinal fluid, the method comprising:
    injecting a drug delivery system (DDS) into a cerebrospinal fluid space at an injection site, the DDS comprising at least one therapeutic agent encapsulated in biodegradable polymers, the therapeutic agent comprising at least one agent for treating or preventing cerebral vasospasms or ischemia, wherein the DDS has a buoyancy relative to the cerebrospinal fluid to allow the DDS to remain at a target area when the ultrasonic energy is removed;
    applying ultrasonic energy proximal to the injection site; and
    creating a directional current of cerebrospinal fluid in the cerebrospinal fluid space using the ultrasonic energy to deliver the DDS to the target area through the cerebrospinal fluid space.

16. The method of claim 15 further comprising guiding delivery of the DDS to the targeted area using the ultrasonic energy.

17. The method of claim 15 wherein the ultrasonic energy is applied in pulsed-wave mode.

18. The method of claim 15, wherein the DDS is one of negatively or neutrally buoyant relative to the cerebrospinal fluid.

19. The method of claim 15, wherein the DDS is non-destructively delivered to the targeted area using the ultrasonic energy.

20. The method of claim 19, wherein the DDS provides extended release of the therapeutic agent, the method comprising adhering the DDS to the target area for extended release thereto.

* * * * *